US008576401B2

(12) United States Patent
Dunsbergen et al.

(10) Patent No.: US 8,576,401 B2
(45) Date of Patent: *Nov. 5, 2013

(54) APPARATUS AND METHOD FOR DETERMINING A CHARACTERISTIC OF A CONSUMABLE

(71) Applicant: Whirlpool Corporation, Benton Harbor, MI (US)

(72) Inventors: Kirk M. Dunsbergen, Stevensville, MI (US); Kaustav Ghosh, Saint Joseph, MI (US); Robert J. Pinkowski, Baroda, MI (US)

(73) Assignee: Whirlpool Corporation, Benton Harbor, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 13/763,905

(22) Filed: Feb. 11, 2013

(65) Prior Publication Data

US 2013/0135621 A1 May 30, 2013

Related U.S. Application Data

(62) Division of application No. 12/890,803, filed on Sep. 27, 2010, now Pat. No. 8,400,638.

(51) Int. Cl.
*G01N 21/55* (2006.01)
*D06B 23/26* (2006.01)

(52) U.S. Cl.
USPC .................................. 356/445; 68/3 R; 8/158

(58) Field of Classification Search
USPC ........ 356/445–448, 432–440; 68/3 R, 12, 18; 8/158, 159
See application file for complete search history.

(56) References Cited

U.S. PATENT DOCUMENTS 8,281,621 B2 * 10/2012 Dunsbergen et al. ........... 68/3 R
2010/0074224 A1 * 3/2010 Mahdi et al. .................. 370/331
2012/0036901 A1 * 2/2012 MacKay et al. .............. 68/17 R
2012/0074224 A1 * 3/2012 Dunsbergen et al. ......... 235/454
2012/0075305 A1 * 3/2012 Dunsbergen et al. ......... 345/422
2012/0075635 A1 * 3/2012 Dunsbergen et al. ......... 356/448
2012/0280032 A1 * 11/2012 Dunsbergen et al. ......... 235/375
2012/0281222 A1 * 11/2012 Dunsbergen et al. ......... 356/445
2013/0048524 A1 * 2/2013 Dunsbergen et al. ...... 206/459.5

* cited by examiner

*Primary Examiner* — Hoa Pham
(74) *Attorney, Agent, or Firm* — Clifton G. Green; McGarry Bair PC

(57) ABSTRACT

The embodiments of the invention relate to a method and apparatus for determining at least one characteristic of a physical resource for use in a physical resource consuming apparatus.

17 Claims, 8 Drawing Sheets

APPARATUS AND METHOD FOR DETERMINING A CHARACTERISTIC OF A CONSUMABLE

CROSS-REFERENCE TO RELATED APPLICATIONS

The present application represents a divisional application of U.S. patent application Ser. No. 12/890,803 entitled "Apparatus and Method for Determining a Characteristic of a Consumable" filed Sep. 27, 2010, pending.

BACKGROUND

A physical resource consuming apparatus, non-limiting examples of which include a refrigerator, a laundry treating appliance, a dishwasher and a beverage dispenser, is an apparatus that consumes at least a portion of a physical resource in the course of performing a cycle of operation. Non-limiting examples of a physical resource include water, a treating chemistry, a fragrance, a flavoring. The physical resource consuming apparatus may have a controller that implements a number of pre-programmed cycles of operation. Information related to one or more properties of the physical resource may be used by the physical resource consuming apparatus in determining how to use a physical resource during one of the pre-programmed cycles of information. The information may be communicated by a user to the physical resource consuming apparatus manually or, alternatively, the information may be determined automatically by the physical resource consuming apparatus.

BRIEF DESCRIPTION

According to one embodiment of the invention, a method of determining at least one characteristic of a treating chemistry inside a removable component having a graphic applied to the removable component in a laundry treating appliance comprises applying a first intensity of light to the graphic and determining a corresponding first reflectance, and applying a second intensity of light to the graphic and determining a corresponding second reflectance, wherein the intensity of the second intensity light is greater than the intensity of the first intensity light and penetrates a surface of the graphic. At least one characteristic of the treating chemistry may be determined from the first and second reflectances.

According to another embodiment of the invention, a physical resource consuming apparatus comprises a physical resource consuming system operating according to a cycle of operation requiring the consumption of at least a portion of a physical resource, a physical resource dispensing system coupled to the physical resource consuming system to dispense a physical resource coupled to the physical resource consuming system and an optical reading system. The physical resource dispensing system may comprise a removable component removably coupled to the physical resource dispensing system and defining a reservoir configured to hold the physical resource and a graphic provided on the removable component and having optically encoded information regarding a characteristic of the physical resource contained in the reservoir. The optical reading system may comprise an illumination source selectively providing illumination at a first intensity and a second intensity onto the graphic when the removable component is coupled to the physical resource dispensing system and a reflectance reader configured to read the reflectance from the graphic when illuminated by the illumination source at the first and second intensity and provide an output indicative of the read reflectance during illumination at the first and second intensities. A controller may be operably coupled to the optical reading system to receive the output and determine at least one operating parameter of the physical resource consuming apparatus as a function of the output.

According to another embodiment of the invention, a method of operating a physical resource consuming apparatus operable according to a cycle of operation and having a removable component supplying the physical resource, and on which is provided a graphic, with the graphic, removable component and physical resource defining a multiple layer composite comprises applying a first intensity of light to the composite and determining a corresponding first reflectance and applying a second intensity of light to the composite and determining a corresponding second reflectance. The intensity of the second intensity light is greater than the intensity of the first intensity light and penetrates a surface of the composite. At least one characteristic of the physical resource may be determined from the first and second reflectances and at least one operating parameter for the physical resource consuming apparatus may be determined as a function of the at least one characteristic.

DESCRIPTION OF EMBODIMENTS OF THE INVENTION

Figure 1:
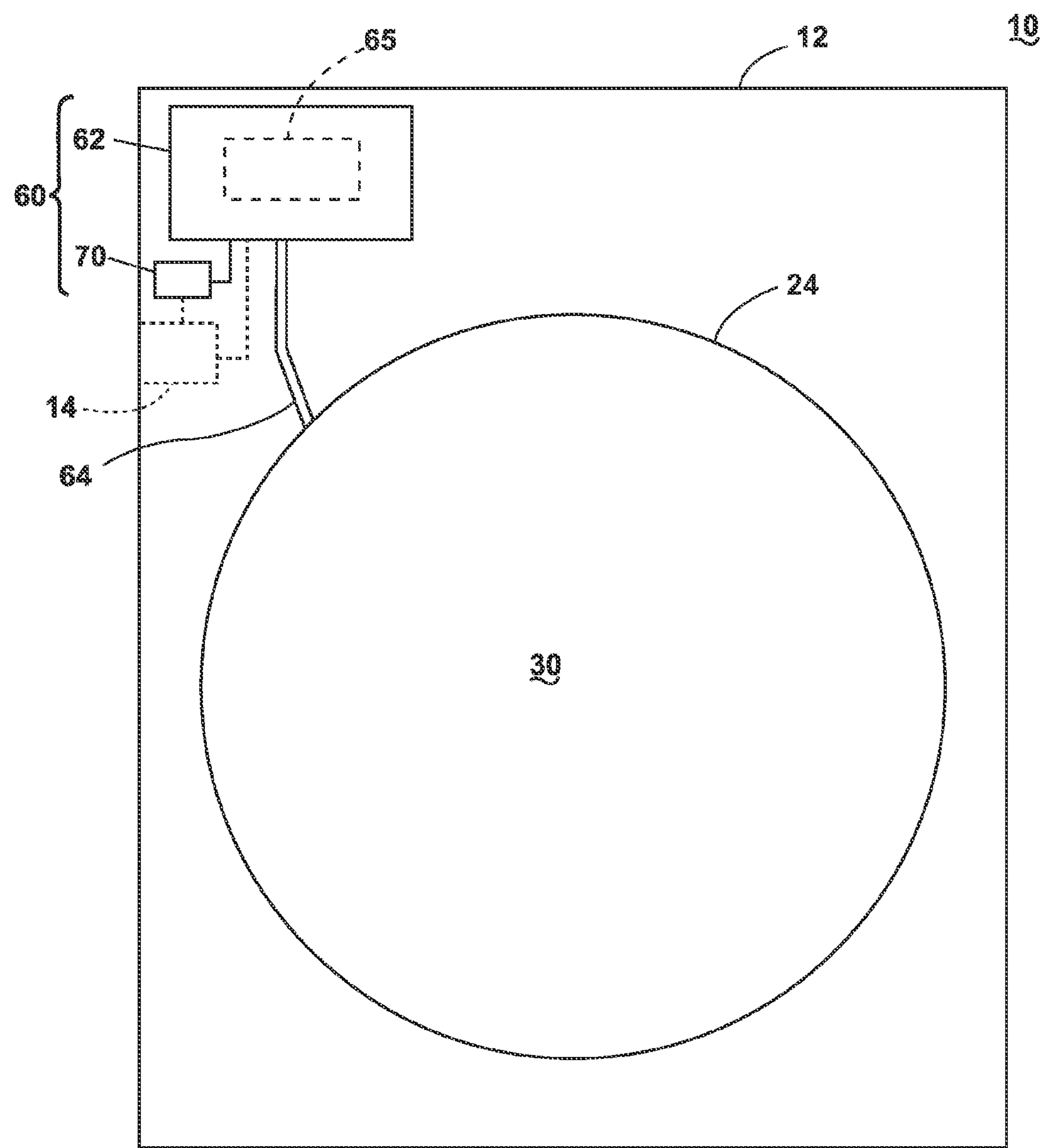
FIG. 1 is a schematic view of a physical resource consuming apparatus according to a first embodiment of the invention.

FIG. 1 illustrates a physical resource consuming apparatus 10 in the form of a laundry treating appliance according to a first embodiment of the invention. Non-limiting examples of a laundry treating appliance include a horizontal or vertical axis clothes washer or clothes dryer; a combination washing machine and dryer; a tumbling or stationary refreshing/revitalizing machine; an extractor; a non-aqueous washing apparatus; and a revitalizing machine. While the physical resource consuming apparatus 10 is illustrated in the form of a laundry treating appliance, the physical resource consuming apparatus 10 may be any appliance which performs a cycle of operation in which a physical resource is consumed. Non-limiting examples of a physical resource consuming apparatus include a refrigerator, a dishwasher and a beverage dispenser.

The physical resource consuming apparatus 10 may include a cabinet 12 having a controller 14 for controlling the operation of the physical resource consuming apparatus 10 to complete a cycle of operation. A rotatable drum 24 may be disposed within an interior of the cabinet 12 to define a treating chamber 30 for receiving laundry to be treated during a cycle of operation.

The physical resource consuming apparatus 10 may also include a physical resource dispensing and identification system 60 operably coupled with the controller 14 for identifying and dispensing a physical resource to the treating chamber 30 during a cycle of operation. The physical resource dispensing and identification system 60 may include a dispensing system 62 fluidly coupled with the treating chamber 30 through a dispensing conduit 64 to dispense a physical resource to the treating chamber 30. The physical resource may be dependent on the type of apparatus and in the case of a laundry treating apparatus may be a treating chemistry, non-limiting examples of which include one or more of the following: water, detergents, fragrances, stiffness/sizing agents, wrinkle releasers/reducers, softeners, antistatic or electrostatic agents, stain repellants, water repellants, rinse aids, antibacterial agents, medicinal agents, vitamins, moisturizers, color fidelity agents, enzymes, surfactants, bleaches, ozone, oxidizing agent, pH adjustors, and combinations thereof. The physical resource may be any type of consumable that is consumed or partially consumed during operation of the physical resource consuming apparatus 10. For example, the physical resource may be a material that is stored and dispensed or a commodity which is utilized during operation of the physical resource consuming apparatus 10, such as electricity or water. In another example, the physical resource may be storable, such as a treating chemistry, or may allow a material to flow through, such as a water filter.

The physical resource consuming and identification system 60 may also include an optical reading system 70 for receiving information related to the physical resource, such as at least one characteristic of the physical resource present within the dispensing system 62. Non-limiting examples of information that may be received from by the optical reading system 70 include information indicative of a cycle of operation, one or more operating parameters of a cycle of operation, an amount to dispense, a time to dispense and a number of times to dispense a physical resource, a presence or absence of a physical resource, a presence or absence of a removable component associated with the physical resource, such as a container for storing a physical resource and/or a filter such as a water or resource filter, a characteristic indicative of a quantity of the physical resource, examples of which include the number of doses remaining, the number of doses dispensed and an amount of the physical resource, identification of the physical resource, a property of the physical resource, e.g., the concentration of the physical resource, and an authentication key. The information may be in the form of optically encoded data capable of being read by the optical reading system 70.

The physical resource may be in any suitable form such that it may be selectively dispensed by the dispensing system 62 to the treating chamber 30 during a cycle of operation. For example, the physical resource may be in gas, liquid, gel or solid form. Additionally, the physical resource may be provided as a removable component which may be selectively coupled and uncoupled with the dispensing system 62. In one example, the removable component may be a storage container for storing the physical component, such as a cartridge or bottle, for example, that may be removably and fluidly coupled with the dispensing system 62 such that the dispensing system 62 may dispense at least a portion of the physical resource from the storage container during a cycle of operation. The removable component may have a reservoir 65 in the form of any suitable interior, such as a hollow or recess within the removable component. The reservoir 65 may include the physical resource or a physical resource processor that may be coupled to the physical resource to process the physical resource. For example, the physical resource processor may include a filter such as a water filter which may be selectively coupled and uncoupled with the dispensing system 62 for filtering water which flows through the water filter, or a resource filter which may process the physical resource such as refrigerator water filter. In the context of a filter, the filter may be both the physical resource, in that it may be replaced over time, and a physical resource processor, in that it processes the water passing through.

The controller 14 may be operably coupled with the optical reading system 70 to determine at least one characteristic of the physical resource present within the dispensing system 62 and control the operation of the physical resource consuming apparatus 10 as a function of the information received from the optical reading system 70. Non-limiting examples of controlling the operation of the physical resource consuming apparatus may include determining or altering one or more of: a cycle of operation, a step of a cycle of operation, operating parameters of a cycle of operation, an amount to dispense, a time to dispense, a number of times to dispense, a presence or absence of a physical resource, a presence or absence of a removable component associated with the physical resource, such as a container for storing a physical resource and/or a filter such as a water or resource filter, a characteristic indicative of a quantity of the physical resource, examples of which include the number of doses remaining, the number of doses dispensed and an amount of the physical resource remaining, an authentication key and a characteristic indicative of a physical property of the physical resource. Non-limiting examples of a physical property of the physical resource include a concentration and an identity of the physical resource.

Figure 2:
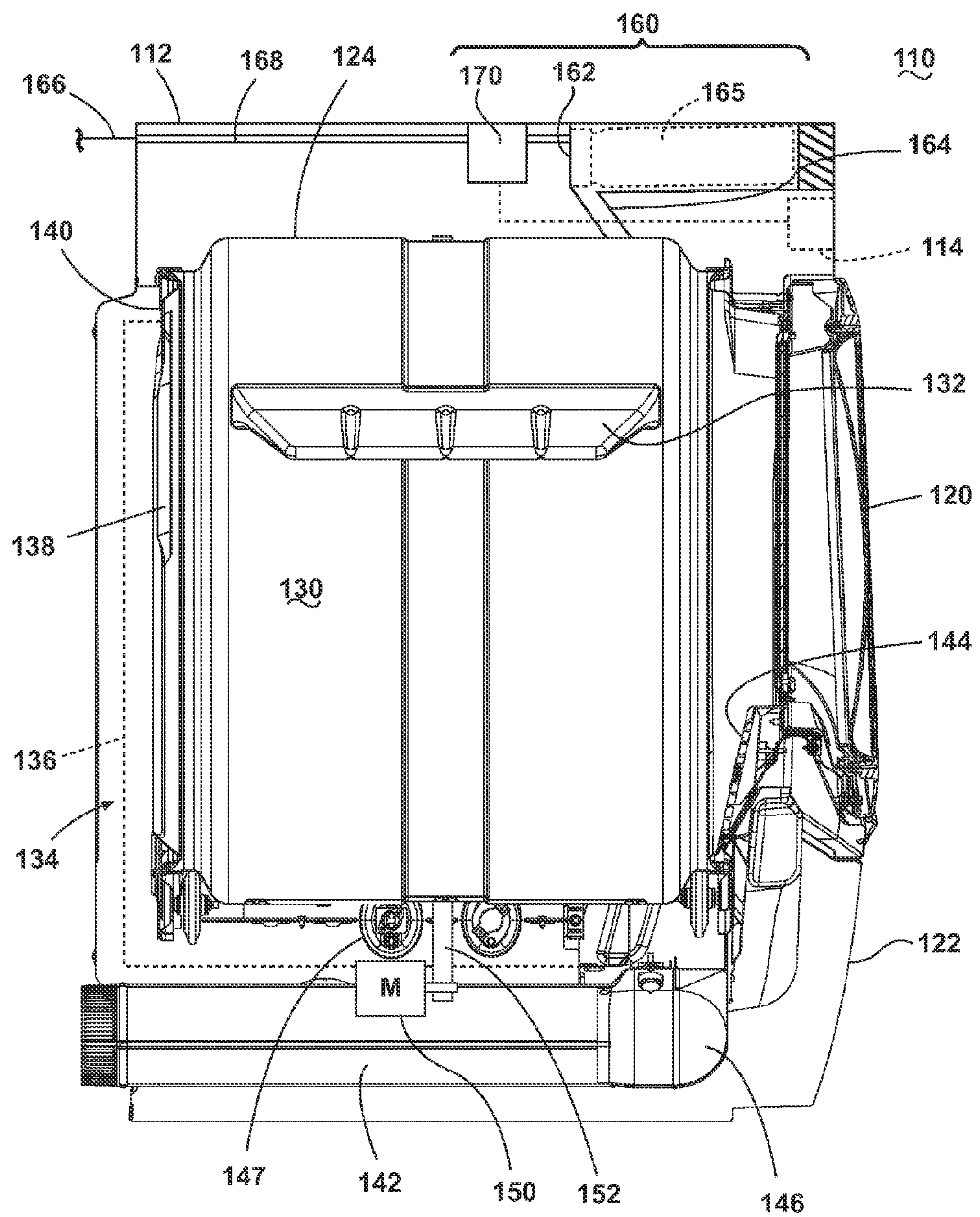
FIG. 2 is a schematic view of a physical resource consuming apparatus in the form of a laundry treating appliance according to a second embodiment of the invention.

FIG. 2 illustrates a second embodiment of the invention where the physical resource consuming apparatus is in the form of a clothes dryer 110 which is similar in structure to the physical resource consuming apparatus 10 in FIG. 1. Therefore, elements in the clothes dryer 110 similar to the physical resource consuming apparatus 10 will be numbered with the prefix 100. The clothes dryer 110 described herein shares many features of a traditional automatic clothes dryer, which will not be described in detail except as necessary for a complete understanding of the invention.

The clothes dryer 110 of the illustrated embodiment may include a cabinet 112 and a controller 114 for controlling the operation of the clothes dryer 110 to complete a cycle of operation. A door 120 may be hingedly mounted to a front wall 122 and may be selectively moveable between opened and closed positions to close an opening in the front wall 122, which provides access to the interior of the cabinet. A control panel or user interface may be integrated with or coupled to the controller 114, and may include one or more knobs, switches, buttons, displays, and the like for communicating with the user, such as to receive input and provide output.

A rotatable drum 124 may be disposed within an interior of the cabinet 112 and define a treating chamber 130 for treating laundry placed therein. The drum 124 may further optionally have one or more lifters or baffles 132. The baffles 132 may be located along the inner surface of the drum 124 defining an interior circumference of the drum 124. The baffles 132 facilitate the tumbling action of the fabric load within the drum 124 as the drum 124 rotates about the rotational axis. Alternatively, a textured surface may be used in place of or in addition to the baffles 132.

An air flow system 134 may be of any conventional type and is provided to draw air into and exhaust air from the treating chamber 130. As illustrated, the air flow system has an inlet duct 136 coupled to the treating chamber by an inlet 138 in a rear bulkhead 140 and an outlet duct 142 coupled to the treating chamber 130 by a lint filter 144. A blower 146 is provided to first draw air through the inlet duct 136, into the treating chamber 130, and to exhaust air from the treating chamber 130 through the outlet duct 142. A heating system 147 may be provided within the inlet duct 136 to heat the air as it passes through on the way to the treating chamber 130.

A motor 150 may be coupled to the drum 124 through a belt 152 (or any other means for indirect drive such as a gearbox) for selectively rotating the drum 124. Non-limiting examples of indirect drive motor systems include three-phase induction motor drives, various types of single phase induction motors such as a permanent split capacitor (PSC), a shaded pole and a split-phase motor. Alternately, the motor 150 may be a direct drive motor, as is known in the art. Non-limiting examples of a direct drive motor include a brushless permanent magnet (BPM or BLDC) motor, an induction motor, etc.

The clothes dryer 110 may also include a physical resource dispensing and identification system 160 operably coupled with the controller 114 for determining at least one characteristic of a physical resource and dispensing the physical resource to the treating chamber 130 during a cycle of operation. The physical resource dispensing and identification system 160 may include a dispensing system 162 fluidly coupled with the treating chamber 130 through a dispensing conduit 164 to dispense a physical resource to the treating chamber 130. The dispensing conduit 164 may be fluidly coupled with the treating chamber 130 in any suitable manner. The physical resource may be a treating chemistry, non-limiting examples of which include one or more of the following: water, detergents, fragrances, stiffness/sizing agents, wrinkle releasers/reducers, softeners, antistatic or electrostatic agents, stain repellants, water repellants, rinse aids, antibacterial agents, medicinal agents, vitamins, moisturizers, color fidelity agents, enzymes, surfactants, bleaches, ozone, oxidizing agent, pH adjustors, and combinations thereof.

The dispensing system 162 may be configured to receive a storage container 165 containing the physical resource and the storage container 165 may be configured to be removably and fluidly coupled with the dispensing system 162 such that the dispensing system 162 may selectively dispense the physical resource during a cycle of operation. Alternatively, the physical resource may be added directly into the dispensing system 162 without the use of a storage container.

Optionally, the dispensing system 162 may be fluidly coupled with a water supply source 166 through a water supply conduit 168 for supplying water to the dispensing system 162 and/or treating chamber 130. The precise physical structure of the dispensing system 162 and storage container is not germane to the invention and may include additional components, such as valves, conduits, mixing chambers, dosing meters, etc, which are not necessary for a complete understanding of the invention.

Figure 3:
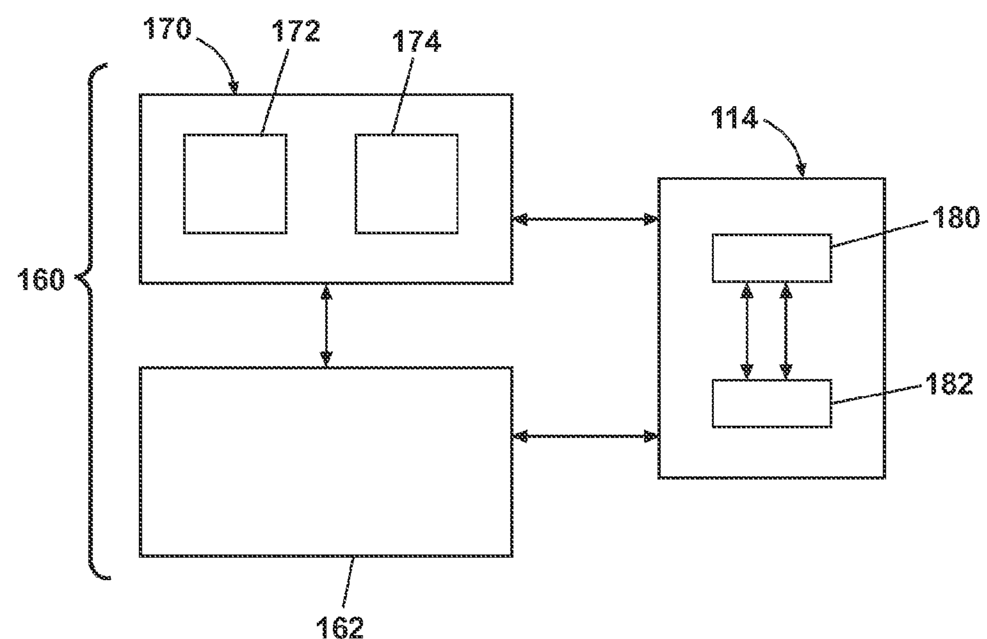
FIG. 3 is a schematic view of a physical resource consuming system and a control system of the laundry treating appliance according to the second embodiment of the invention.

Referring now to FIG. 3, the optical reading system 170 may include one or more illumination sources 172 for illuminating the physical resource and/or the physical resource container 165 and one or more detectors 174 for receiving the illumination reflected and/or transmitted by the physical resource and/or the physical resource container 165.

The optical reading system 170 may be coupled with the dispensing system 160 in any suitable manner such that the optical reading system 170 is capable of illuminating and receiving reflected illumination from the physical resource and/or the physical resource container. Non-limiting examples of illumination sources include an LED light, an incandescent bulb, a fluorescent bulb, an infrared light, an ultraviolet light, a Xenon flash lamp, a Mercury flash lamp, a laser and combinations thereof. Non-limiting examples of detectors include a CCD detector, a CMOS camera, a photodetector, a photodiode, an avalanche detector, an InGaAs detector, a photomultiplier tube, a silicon detector and combinations thereof. The illumination light from the illumination sources may include infrared, visible, ultraviolet, and other entire electromagnetic spectrum.

The optically encoded data carried by the physical resource and/or the physical resource container may be in the form of illumination data reflected, absorbed or transmitted from the physical resource and/or the physical resource container when the physical resource and/or the physical resource container is illuminated by the illumination source 172. The detector 174 may be capable of reading the illumination data received from the physical resource and/or the physical resource container 165 for determining at least one characteristic of the physical resource.

The illumination source 172 may be a single illumination source configured to provide illumination at least two different intensities and/or at least two different wavelengths. Alternatively, the illumination source 172 may be in the form of multiple illumination sources configured to provide illumination at different intensities and/or different wavelengths. The light provided from the illumination source may be provided at a predetermined polarity, with the polarity varying with the intensity and/or wavelength.

The controller 114 may be provided with a memory 180 and a central processing unit (CPU) 182. The memory 180 may be used for storing the control software comprising executable instructions that is executed by the CPU 182 in completing one or more cycles of operation using the clothes dryer 110 and any additional software. The memory 180 may also be used to store information, such as a database or table, and to store data received from one or more components of the clothes dryer 110 that may be communicably coupled with the controller 114. The database or table data may be used to store the various operating parameters for the one or more cycles of operation, including factory default values for the operating parameters and any adjustments to them by the control system or by user input.

The controller 114 may be operably coupled with one or more components of the clothes dryer 110 for communicating with and controlling the operation of the component to complete a cycle of operation, such as sensors, actuators, valves, latches, locks, and many other components. For example, the controller 114 may be coupled with the motor 150 for controlling the direction and speed of rotation of the drum 124 and the dispensing system 162 for dispensing a physical resource during a cycle of operation. The controller 114 may also be coupled with the user interface for receiving user selected inputs and communicating information to the user.

The controller 114 may also receive input from one or more sensors, which are known in the art and not shown for simplicity. Non-limiting examples of sensors that may be communicably coupled with the controller 114 include: a one or more temperature sensors, a moisture sensor, a weight sensor, a position sensor and a motor torque sensor.

The controller 114 may also be operably coupled with the dispensing system 162 and the optical reading system 170 to receive information related to the physical resource and to control the operation of the clothes dryer 110 as a function of the information. The optical reading system 170 may receive the illumination data from the physical resource and/or the physical resource container 165 and communicate the illumination data with the controller 114 for determining at least one characteristic of the physical resource. Alternatively, the optical reading system 170 may also include a memory and a central processing unit for storing the illumination data and determining at least one characteristic of the physical resource. The optical reading system 170 may then communicate the determination related to at least one characteristic of the physical resource with the controller 114 and the controller 114 may use the information to control the operation of the clothes dryer 110.

Figure 4:
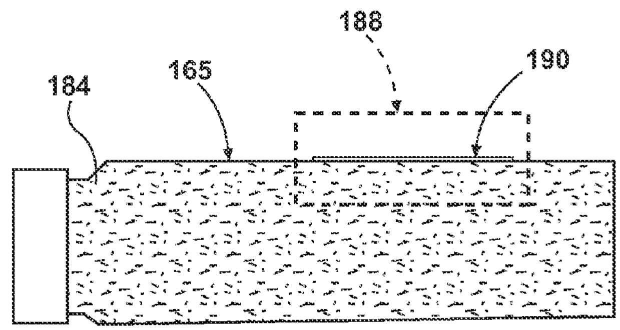
FIG. 4 is a cross-sectional view of a physical resource storage container according to a third embodiment of the invention.

Referring now to FIG. 4, a physical resource 184 may be stored in the physical resource storage container 165 for dispensing before, during or after a cycle of operation during operation of the clothes dryer 110. As discussed above, the physical resource storage container 165 may be configured to selectively and fluidly couple with the dispensing system 162 to dispense at least a portion of the physical resource 184 for use during operation of the clothes dryer 110. The physical resource storage container 165 may further include a composite 188 having optically encoded information that may be read by the optical reading system 170 and used by the controller 114 to determine at least one characteristic of the physical resource 184.

Figure 5:
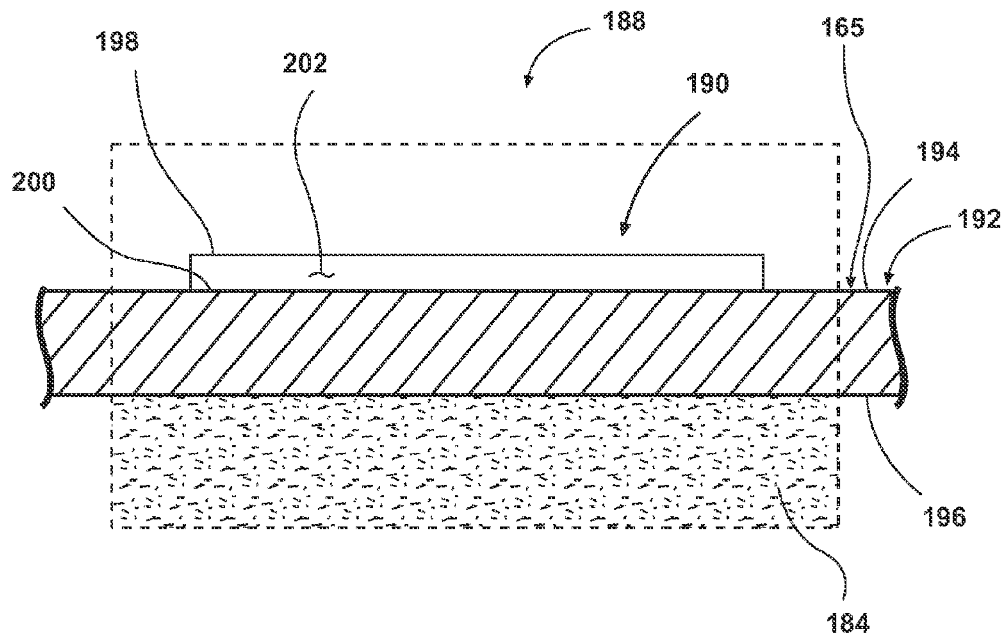
FIG. 5 is a cross-sectional view of a composite for use in a physical resource consuming apparatus according to a fourth embodiment of the invention.

Referring now to FIG. 5, the composite 188 is illustrated in exaggerated detail for the purposes of discussion only and is not meant to limit the embodiments of the invention in any manner. The elements of the composite 188 have not been drawn to scale and have been exaggerated for clarity for the purposes of discussion. The composite 188 may include multiple layers which may include one or more of at least a portion of the physical resource 184 inside the physical resource storage container 165, a graphic 190 and at least a portion of a container body 192 defining the container 165 within which the physical resource 184 is stored.

While the embodiments of the invention will be described in the context of a composite 188 including a graphic 190, a container body 192 and a physical resource 184, it is also within the scope of the invention for the composite 188 to include just a graphic 190 and a physical resource 184. For example, when the physical resource 184 is a solid, the graphic 190 may be located directly on the physical resource 184. In the embodiment in which the physical resource 184 is stored in the container 165, the graphic 190 may be located generally on an outer surface 194 of the container body 192. It is also within the scope of the invention for the graphic 190 to be located on an inner surface 196. Alternatively, a portion of the graphic 190 may be located on the outer surface 194 and another portion of the graphic may be located on the inner surface 196. In another example, the graphic 190 may be integrated into the container body 192, such as by inset molding, for example.

Still referring to FIG. 5, the graphic 190 may include an upper portion 198, a lower portion 200 opposite the upper portion 198 and adjacent to the outer surface 194 of the container body 192, and a medial portion 202 located between the upper portion 198 and the lower portion 200. Each of the upper portion 198, lower portion 200 and medial portion 202 may have any thickness and may be formed from a single layer of atoms or multiple layers of atoms. For example, the upper portion 198 may be considered to be a single layer of atoms on the surface of the graphic 190 farthest from the container body 192. Alternatively, the upper portion 198 may be considered to be formed from multiple, adjacent layers of atoms farthest from the container body 192. In both examples, the upper portion 198 may be considered the surface of the graphic 190 while the lower portion 200 and/or the medial portion 202 may be considered an interior of the graphic 190. Regardless of the orientation of the container 165, the lower portion 200 is considered the portion adjacent to the cartridge body 192 and the upper portion 198 is considered the portion opposite the lower portion 200, farthest away from the container body 192. It is also within the scope of the invention for the upper portion 198, lower portion 200 and medial portion 202 to have the same or different thicknesses.

The graphic 190 may be formed from a single material, or alternatively, the graphic 190 may include multiple layers of material located between the upper portion 198 and the lower portion 200. For example, the graphic 190 may be formed from a single material such that the upper portion 198, lower portion 200 and medial portion 202 are defined as a function of their relative spatial relationship to one another. In another example, the graphic 190 may be formed from a single type of material having one or more physical properties that differs between at least two of the upper portion 198, lower portion 200 and medial portion 202. In another example, the graphic 190 may be formed from multiple layers of different material and the upper portion 198 would be formed from at least a portion of the layer farthest from the container body 192 and the lower portion 200 would be formed from at least a portion of the layer adjacent the container body 192, with at least two of the multiple layers of material differing from one another by at least one or more physical properties. Non-limiting examples of such physical properties include thickness, texture, color, refractivity, reflectivity, absorbance, transmittance, index of refraction and optical polarity. The medial portion 202 may be a single layer or may comprise multiple layers disposed between the upper and lower portions 198, 200.

The graphic 190 may be coupled with the cartridge body 192 using any suitable mechanical or non-mechanical fastener. Examples of a suitable mechanical fastener include pins and tabs. Examples of suitable non-mechanical fasteners include adhesives, welding and ultrasonic welding. In another example, the graphic 190 may be printed directly on the container body 192 or the physical resource 184 using known techniques. In yet another example, at least a portion of the container body 192 may be wrapped in shrink wrap or other polymeric plastic film and the graphic may be printed or fastened to the film. In one embodiment of the invention, the graphic 190 may be in the form of a label coupled with the cartridge body 192. In another embodiment, the graphic 190 may be printed onto the container body 192 or printed onto a wrapper covering at least a portion of the container body 192. The graphic 190 can be any type of visible and/or non-visible indicia such as alphanumeric symbols, shapes, patterns or symbols.

The container body 192 may be formed from any suitable polymeric material. For example, the container body 192 may be formed from polyethylene terephthalate, high and low density polyethylene and polypropylene. It is also within the scope of the invention for different portions of the container body 192 to be formed from different materials. For example, a majority of the container body 192 may be formed from one material while the portion of the container body 192 adjacent the graphic 190 may be formed from a different material having one or more different physical properties. The container body 192 and/or a surface of the container body 192 may be formed from a material or may be combined with a material that provides at least a portion of the container body 192 with a predetermined optical characteristic for optically encoding data related to a presence and/or characteristic of the physical resource. Non-limiting examples of physical properties that can provide a predetermined optical characteristic include color, thickness, texture, refractivity, reflectivity, absorbance, transmittance, index of refraction and optical polarity.

The composite 188 may be considered a multi-layer composite as the graphic 190, container body 192 and physical resource 184 may each be considered a layer in the composite 188. In addition, each of these layers, the graphic 190, cartridge body 192 and the physical resource 184, may also include multiple layers. One or more of the layers of the composite 188 may be formed from a material having one or more physical properties such that the illumination reflected, absorbed or transmitted by the layer when illuminated by the illumination source 172 is distinguishable by the detector 174 from the illumination reflected, absorbed or transmitted by a different layer of the composite 188 when illuminated by the illumination source 172. Differences in reflectance detected from one or more layers of the composite 188 when illuminated by the illumination source 172 may be used as optically encoded data that the controller 114 may use to determine at least one characteristic of the physical resource 184.

Any changes in the physical properties of the one or more layers of the composite 188 may provide different optical characteristics when illuminated by the illumination source 172. For example, one or more of the layers of the composite 188 may have predetermined textures, combined with any suitable optical method, to provide predetermined optical characteristics when illuminated by the illumination source 172. In case predetermined textures for the one or more of the layers of the composite 188 is modified using, for example, any physical or chemical treatments, different optical characteristic from the composite 188 may be provided when illuminated by the illumination source 172. And the illumination reflected, absorbed or transmitted by the layer after the texture modification may be distinguishable by the detector 174 from the illumination reflected, absorbed or transmitted by the layer before the texture modification. Physical properties concerning this invention that would vary due to a change in texture and would change the required optical characteristics is differing degrees of specular and diffuse reflectance between the different textures for light of the same intensity with surfaces designed to have mostly specular reflectance to surfaces having a combination of specular and diffuse reflectance to surfaces having mostly diffuse reflectance.

Alternatively, one or more of layers in the composite 188 may reflect, absorb or transmit the light having a first predetermined polarity in a distinguishable way than the light having a second predetermined polarity. For example, the surface or any one or more of the layers of the graphic or removable component in a composite 188 may selectively reflect, absorb or transmit the light having a first predetermined polarity in a way that may be distinguished from the light having a second predetermined polarity, where the first and the second predetermined polarity may vary with the intensity and/or wavelength.

The previously described physical resource consuming apparatuses 10 and 110 may be used to implement one or more embodiments of a method of the invention. Several embodiments of the method will now be described in terms of the operation of the clothes dryer 110. While the methods are described with respect to the clothes dryer 110, the methods may also be used with the physical resource consuming apparatus 10 of the first embodiment of the invention. The embodiments of the method function to determine at least one of characteristic of a physical resource in the dispensing system 162 and to control the operation of the clothes dryer 110 as a function of the determination. Non-limiting examples of controlling the operation of the physical resource consuming apparatus may include determining or altering one or more of: a cycle of operation, a step of a cycle of operation, operating parameters of a cycle of operation, an amount to dispense, a time to dispense, a presence or absence of a physical resource, a presence or absence of a removable component associated with the physical resource, such as a container for storing a physical resource and/or a filter such as a water or resource filter, a number of times to dispense, a characteristic indicative of a quantity of the physical resource, examples of which include the number of doses remaining, the number of doses dispensed and an amount of the physical resource remaining, and a characteristic indicative of a physical property of the physical resource. Non-limiting examples of a physical property of the physical resource include a concentration and an identification of the physical resource.

Figure 6:
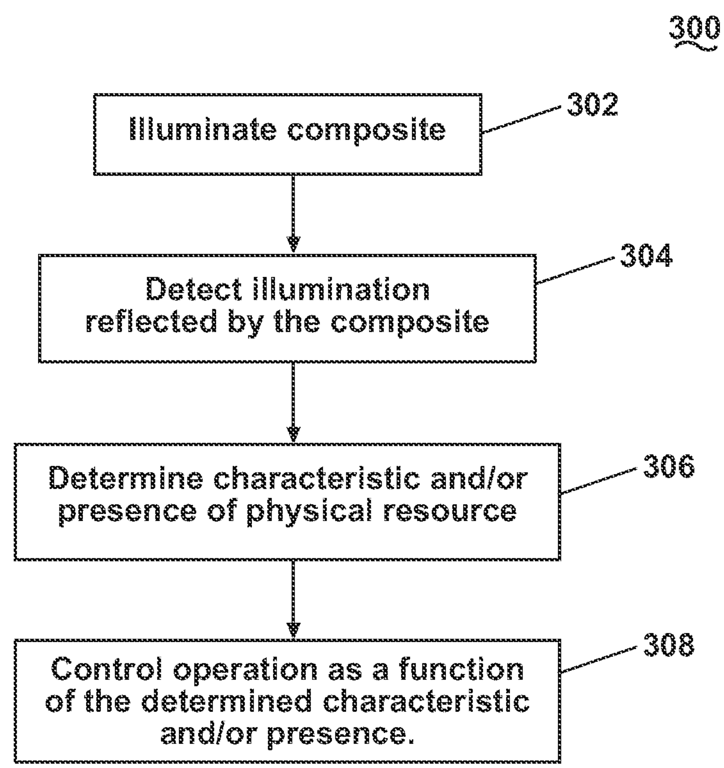
FIG. 6 is a flow chart illustrating a method for determining a presence and/or a characteristic of a physical resource according to a fifth embodiment of the invention.

FIG. 6 illustrates a method 300 for determining at least one characteristic of a physical resource according to an embodiment of the invention. The method 300 assumes that a user has placed the physical resource 184 stored in the container 165 including the composite 188 into the dispensing system 162 of the clothes dryer 110. At 302 the controller 114 may control the optical reading system 170 to illuminate the composite 188 with the illumination source 172. The controller 114 may control the optical reading system 170 automatically, such as when the presence of an item in the dispensing system 162 is detected or when a user selects an operating cycle, for example. Alternatively, the optical reading system 170 may be initiated manually by the user.

At 304 the detector 174 of the optical reading system 170 may detect the illumination reflected by the composite 188 that was illuminated at 302. The controller 114 may then use the illumination data from the detector 174 at 306 to determine at least one characteristic of the physical resource 184. At 308, the controller 114 may use the determined at least one characteristic of the physical resource 184 determined at 306 to control the operation of the clothes dryer 110 as a function of the determined at least one characteristic of the physical resource. The illumination and detection at 302 and 304 may be repeated any number of times to determine the one or more characteristics of the physical resource 184 at 306.

Figure 7:
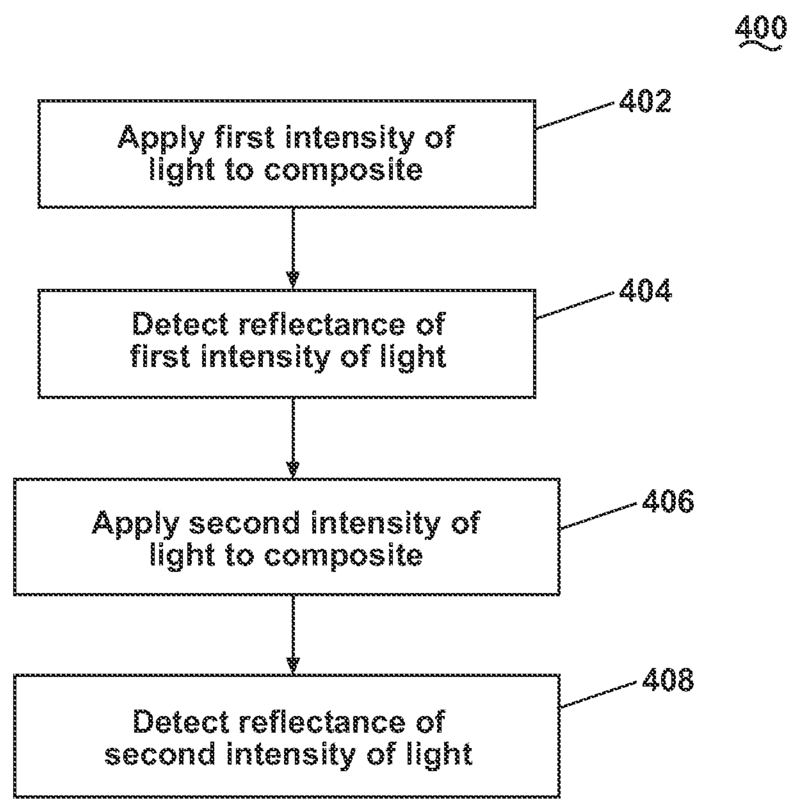
FIG. 7 is a flow chart illustrating a method for illuminating a composite according to a sixth embodiment of the invention.

FIG. 7 illustrates a method 400 for illuminating the composite 188 and detecting the illumination reflected by the composite 188. The method 400 may be used at 302 and 304 of the method 300 illustrated in FIG. 6. Alternatively, the method 400 may be initiated independently of the method 300.

The method starts at 402 by illuminating the composite 188 with light having a first intensity. At least a portion of the first intensity light reflected by the composite 188 may be detected by the detector 174 at 404. At 406 the illumination source 172 may illuminate the composite 188 with light having a second intensity, which is different than the first intensity. At least a portion of the second intensity light reflected by the composite 188 may be detected by the detector 174 at 408.

It is within the scope of the invention for the order of the method 400 to be initiated sequentially from 402 to 404 to 406 to 408 or, alternatively, one or more elements 402, 404, 406 or 408 of the method 400 may be conducted simultaneously.

The illumination source 172 may be configured to illuminate the composite with first and second intensity light at 402 and 406 such that the first and second intensity lights penetrate to different layers or regions of the composite 188. The different layers of the composite 188 which are intended to reflect the first and second intensity lights may be configured to have at least one different physical property such that the reflectance of the first and second intensity lights optically encode information related to the physical resource 184. Non-limiting examples of such physical properties include thickness, texture, color, refractivity, reflectivity, absorbance, transmittance, index of refraction and optical polarity. For example, the illumination source 172 may be configured such that the first intensity light penetrates and is primarily reflected by the graphic 190 while the second intensity light penetrates and is primarily reflected by the physical resource 184. The controller 114 may use the information regarding at least one of the thickness, texture, color, refractivity, reflectance, absorbance, transmittance, wavelength (color) and intensity of the reflected light detected by the detector 174 when the composite 188 is illuminated by the first and second intensity lights to determine at least one characteristic of the physical resource 184.

While the embodiments of the invention are described in the context of light being reflected by a single layer of the composite 188, it is understood that not all of the light of a given intensity will be reflected by a single layer of the composite 188. Some of the light may be reflected by other layers of the composite 188 and some of the light may be reflected and scattered by components of the composite 188 and dispensing system 162 away from the detector 174. By primarily reflected, it is meant that the light reflected by the layer is such that a physical property of the layer can be identified and/or distinguished from at least one other layer of the composite 188 as a function of the reflected light detected by the detector 174.

Figure 8:
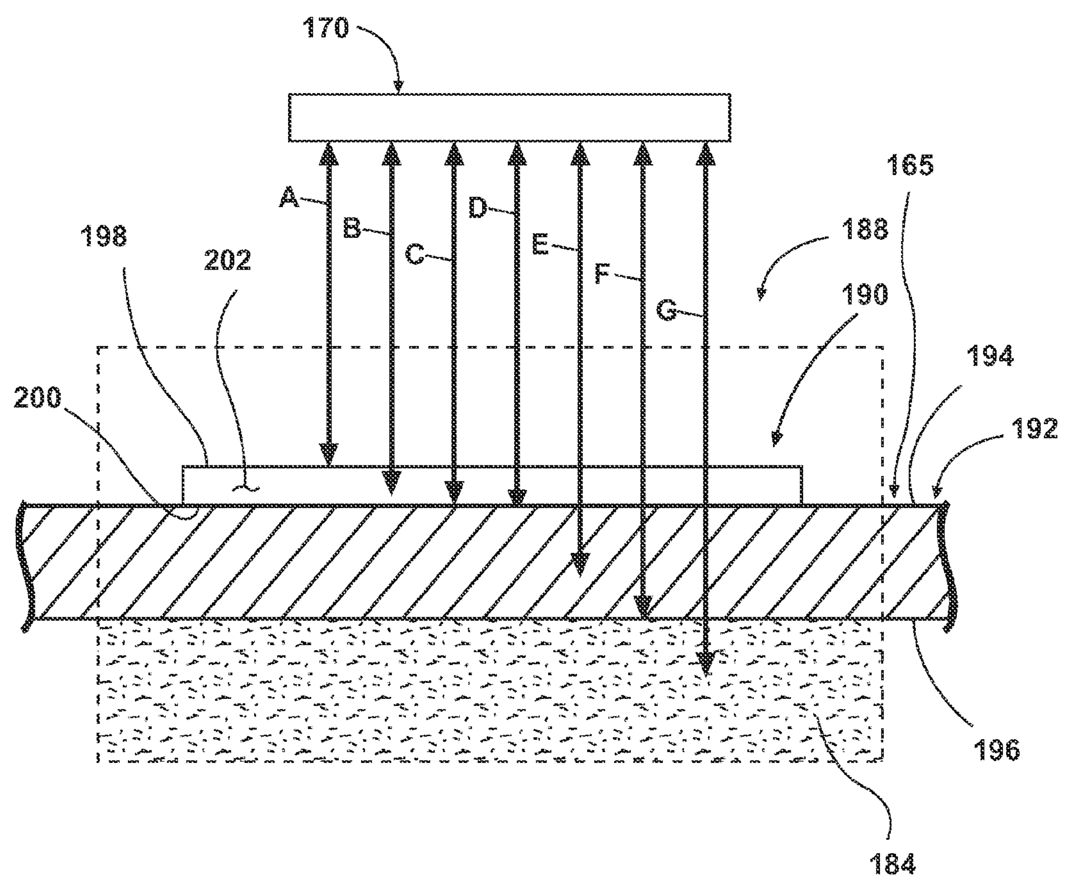
FIG. 8 is a schematic illustration of illumination and reflectance from a composite according to a seventh embodiment of the invention.

FIG. 8 is a schematic illustration of the different layers of composite 188 that may be illuminated by the first and second intensity lights at 402 and 406 of the method 400. The different layers of the composite 188 are illustrated for the purposes of discussion only and are not meant to limit the invention in any manner, as it is understood that the composite 188 can be considered to have fewer, additional or different layers. Lines A through G illustrate the illumination of and reflectance from seven different layers or regions of the composite 188 that may be illuminated by the first and second intensity lights at 402 and 406 and reflected back to the detector 174 at 404 and 408. The optical reading system 170 may be configured to illuminate and detect the reflectance from any combination of first and second lights A through G. Line A illustrates illumination of and reflectance from the upper portion 198 of the graphic 190, line B illustrates illumination of and reflectance from the medial portion 202 of the graphic 190 and line C illustrates illumination of and reflectance from the lower portion 200 of the graphic 190. Line D illustrates illumination of and reflectance from a region of the composite 188 that may include the outer surface 194 of the cartridge body 192 and/or an interface between the container body 192 and the graphic 190. Line E illustrates illumination of and reflectance from an interior of the container body 192 and line F illustrates illumination of and reflectance from the inner surface 196 of the container body 192. Alternatively, line F may illustrate illumination of and reflectance of an interface between the inner surface 196 and the physical resource 184. Line G illustrates illumination of and reflectance from the physical resource 184.

As illustrated in FIG. 8, the optical reading system 170 may be positioned relative to the container 165 such that when there is physical resource 184 present in the container 165, there is no air gap between the container body 192 and a surface of the physical resource 184. For example, the optical reading system 170 may be positioned along a lower side or a bottom of the container 165. It is also within the scope of the invention that the composite 188 include some air between one or more of the layers of the composite 188, such as between the surface of the physical resource 184 and the container body 192. The optical reading system 170 may be configured such that the illumination is capable of being transmitted through any air gap between the layers of the composite 188 to reach the intended layer.

The illumination source 172 may be configured to illuminate any one of the layers of the composite 188 illustrated by lines A through G in FIG. 8 with the first intensity light at 402 and any one of the other regions illustrated by lines A through G with the second intensity light at 404. For example, the first intensity light may be light of a lower intensity than the second intensity light. The higher intensity light may be used to transmit light through one or more of the layers of the composite 188 which are nearest the detector 174 to reach a layer that is located deeper within the composite 188 and farther away from the optical reading system 170. Higher intensity light has a greater capacity to travel farther and reach regions that are farther away from the optical reading system 170 than lower intensity light. The amount of light that is transmitted a predetermined distance from the illumination source 172 is greater the higher the intensity of light emitted from the illumination source 172. The illumination source 172 and composite 188 may be configured such that higher intensity light is capable of being transmitted through one or more layers of the composite 188 to a layer deeper within the composite 188 such that the optical data encoded in the deeper layer may be reflected back to the detector 174. In this manner, the intensity of light emitted from the illumination source 172 may be varied to illuminate different layers of the composite 188 to retrieve the optically encoded data that may be contained within the different layers of the composite 188.

While the method 400 is described in the context of using light of different intensities to illuminate and retrieve optically encoded data from different layers of the composite 188, any suitable optical method may be used for illuminating the different layers of the composite 188 and one or more layers of the composite 188 may be configured such that the optically encoded data may be retrieved using said optical method. In one example, the polarity of the illumination light may be varied such that different layers of the composite 188 are illuminated. One or more layers of the composite 188 may be configured to transmit light of a first polarity while reflecting light of a second polarity. Specifically, the polarity of the illumination light having varying intensities and/or frequencies may be varied such that different layers of the graphic 190 are illuminated. One or more layers of the graphic 190 may be configured to transmit light of a first polarity while reflecting light of a second polarity. In another example, the frequency of light may be varied such that different layers of the composite 188 are illuminated. One or more layers of the composite 188 may be configured to transmit light of a first frequency while reflecting light of a second frequency. In still another example, the wavelength of the illumination light may be varied to illuminate different layers of the composite. One or more layers of the composite 188 may be configured to transmit light of a first wavelength while reflecting light of a second wavelength. In yet another example, illumination light having multiple wavelengths, where multiple wavelengths include wavelength that may vary sequentially, may be configured to illuminate different layers of the composite 188. One or more layers of the composite 188 may be configured to transmit light having a first portion of the multiple wavelengths while reflecting light having a second portion of the multiple wavelengths. In still yet another example, illumination light having multiple wavelengths and varying intensity and/or frequencies and may be used for illuminating the different layers of the composite 188. One of more layers of the composite 188 may be configured to transmit light of a first portion of the multiple wavelengths, a first intensity and/or a first frequency, while reflecting a second portion of the multiple wavelengths, a second intensity and/or a second frequency.

In addition, while the method 400 is described in the context of illuminating the composite 188 with first and second intensities, the composite 188 may be illuminated with any number of different intensities of light such that any number of layers of the composite 188 are illuminated and may reflect optically encoded data back to the detector 174. Similarly, the composite 188 may be illuminated with illumination having a plurality of polarities, frequencies and wavelengths such that any number of layers of the composite 188 may be illuminated and reflect optically encoded data back to the detector 174.

Figure 9:
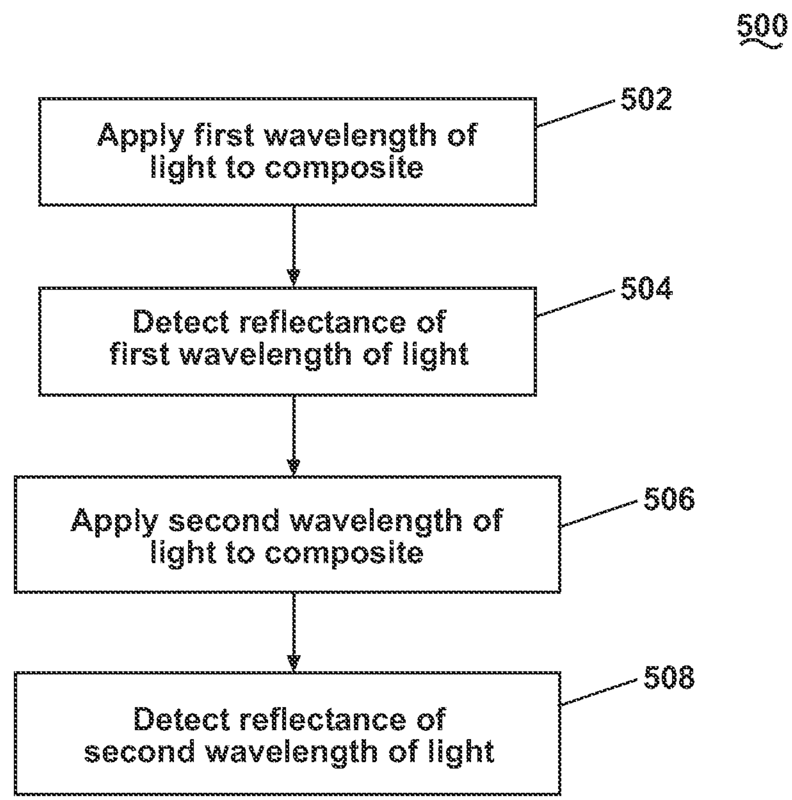
FIG. 9 is a flow chart illustrating a method for illuminating a composite according to an eighth embodiment of the invention.

Alternatively to, or in combination with, the method 400, a method 500 may be used to illuminate the different layers of the composite 188 illustrated by lines A through G in FIG. 8 using light having first and second wavelengths, with the second wavelength being different from the first. As illustrated in FIG. 9, the method starts at 502 by illuminating the composite 188 with light having a first wavelength. At least a portion of the first wavelength light reflected by the composite 188 may be detected by the detector 174 at 504. At 506 the illumination source 172 may illuminate the composite 188 with light having a second wavelength, which is different than the first wavelength. At least a portion of the second wavelength light reflected by the composite 188 may be detected by the detector 174 at 508. The first and second wavelength light may have the same or different intensities.

The method 500 may be used at 302 and 304 of the method 300 illustrated in FIG. 6 and may also be optionally combined with the method 400 of FIG. 7. Alternatively, the method 500 may be initiated independently of the methods 300 and 400.

The materials of the composite 188 may be configured such that one or more layers of the composite 188 are capable of reflecting at least a portion of the first wavelength light while transmitting all or most of the second wavelength of light to one or more other layers of the composite 188. For example, referring again to FIG. 8, the first wavelength light may be used to illuminate the upper portion 198 of the graphic 190 and the upper portion 198 may be configured so as to reflect at least a portion of the first wavelength light back to the detector 174. The upper portion 198 may also be configured to transmit the second wavelength light such that at least some of the second wavelength light is not reflected by the upper portion 198, but transmitted through the composite 188 to one of the internal layers of the composite 188 as illustrated by lines B through G of FIG. 8. For example, the composite 188 may be configured such that light having a wavelength corresponding to red light is primarily reflected by the upper portion 198 of the graphic 190 and light having a wavelength corresponding to green light is transmitted through the upper portion 198 to any of the internal layers of the composite 188 where it may be reflected back to the detector 174.

The composite 188 is configured such that the reflectance of the different layers of the composite at different wavelengths of light may be used to optically code data related to at least one characteristic of the resource 184 in a manner similar to that described above for the method 400 illustrated in FIG. 7. The reflectance from the composite 188, either of the first and second intensity light detected at 404 and 408 of the method 400 illustrated in FIG. 6 or the first and second wavelengths of light detected at 504 and 508 of the method 500 illustrated in FIG. 9, may be used to determine an output that may be used by the controller 114 to determine at least one characteristic of the physical resource 184 at 306 of the method 300 illustrated in FIG. 6.

For example, the controller 114 may include a coding matrix that relates the output of the reflectance readings from the detector 174 to at least one characteristic of the resource 184. The output may be a function of the reflectance detected by the detector 174 when the composite 188 is illuminated with first and second intensities and/or first and second wavelengths of light. The output may then be used by the controller 114 to determine at least one characteristic, non-limiting examples of which include: information indicative of a cycle of operation, one or more operating parameters of a cycle of operation, an amount to dispense, a time to dispense and a number of times to dispense a physical resource, a presence or absence of a physical resource, a presence or absence of a removable component associated with the physical resource, such as a container for storing a physical resource and/or a filter such as a water or resource filter, a characteristic indicative of a quantity of the physical resource, examples of which include the number of doses remaining, the number of doses dispensed and an amount of the physical resource, identification of the physical resource, a property of the physical resource and an authentication key.

In one example, the output may be a function of the difference in the light reflected from the composite 188 when illuminated with the first light and the second light having first and second intensities and/or wavelengths. Alternatively, the output may be a function of the absence of reflection, the absence of a predetermined amount of reflection and/or the absence of reflection at a predetermined wavelength from the composite 188 when illuminated with the first light and the second light. In another example, the output may be a function of the presence of an unexpected reflectance during illumination by the illumination source 172.

When only a first light and a second light having first and second intensities and/or wavelengths is used, the composite 188 may optically encode 2 data bits that both may be used to encode for at least one characteristic of the physical resource. Alternatively, 1 data bit may be used to characterize the physical resource and the second data bit may be used as authorization for use of the physical resource in the physical resource consuming apparatus, for example. Additional data bits may be achieved by optically encoding additional data into the composite that may be retrieved by illuminating the composite 188 with light having additional intensities and/or wavelengths. In another embodiment, the identification may not include two bits of data. For example, the light could be focused such that a first light having a single intensity and/or wavelength may read a first bar code on the top layer of the composite 188 and then a second light having a second intensity and/or wavelength may read a second bar code on an interior layer of the composite 188, where the composite 188 may contain multiple reflectances from codes, and codes may be limited in size and/or space.

In another example, the number of doses of the physical resource remaining and/or used may be determined as a function of the illumination reflected from the physical resource 184. In the embodiment where the physical resource comprises a liquid or gel stored within a container 165, the location of the detector 174 relative to the physical resource 184 may be configured such that as the physical resource 184 is consumed, the distance between the detector 174 and the surface of the physical resource 184 increases. As the distance between the detector 174 and the surface of the physical resource 184 increases, the intensity of the light reflected back to the detector 174 from the physical resource 184 decreases. The controller 114 may then be programmed to determine the number of doses remaining and/or used as a function of the change in reflectance from the physical resource 184 when the physical resource is illuminated with a light having a predetermined intensity and/or wavelength. The controller 114 may then communicate information regarding the status of the physical resource 184 with the user through the user interface. This information may also be combined with other optically encoded data retrieved from the composite 188 to control the operation of the clothes dryer 110.

Alternatively, in another embodiment where the physical resource 184 is in the form of individual discs or pellets that are dispensed by the dispensing system 162, individual discs may have information related to the number of doses remaining or used optically encoded onto the discs by the composite 188. For example, in an embodiment in which the discs are dispensed sequentially, one or more discs may be optically encoded to indicate to the controller 114 when a predetermined number of doses is remaining or has been used and the controller 114 may communicate this information with the user through the user interface.

In another embodiment, the physical resource 184 and/or the container 165 may be optically encoded with the total number of doses of the physical resource 184. The controller 114 may be programmed to determine the total number of doses of the physical resource 184 from the optically encoded data and track the number of doses dispensed during operation of the clothes dryer 110. Based on the total number of doses determined from the optically encoded data and the number of doses dispensed, the controller 114 may be programmed to determine the number of doses remaining and communicate this information with a user. In another example, the controller 114 may be programmed to alert the user when all of the doses have been dispensed and no more doses remain or not enough of the physical resource remains to dispense a dose of a predetermined size. The controller 114 may communicate the dosage information to the user in any suitable manner, such as visually, through a user interface or other display, or audibly.

The apparatuses and methods described herein may provide a simple and inexpensive solution for encoding information relating to at least one characteristic of a physical resource and controlling the operation of a physical resource consuming apparatus as function of the encoded information. The encoded information may provide the physical resource consuming apparatus with improved performance during a cycle of operation. The encoded information may be used by the apparatus to control the operation of the apparatus such that the physical resource is used by the apparatus in the manner in which it was designed to achieve optimal or desired results. The encoded information may also be used to prevent the use of unauthorized or incompatible physical resources.

To the extent not already described, the different features and structures of the various embodiments may be used in combination with each other as desired. That one feature may not be illustrated in all of the embodiments is not meant to be construed that it cannot be, but is done for brevity of description. Thus, the various features of the different embodiments may be mixed and matched as desired to form new embodiments, whether or not the new embodiments are expressly described.

While the invention has been specifically described in connection with certain specific embodiments thereof, it is to be understood that this is by way of illustration and not of limitation. Reasonable variation and modification are possible within the scope of the forgoing disclosure and drawings without departing from the spirit of the invention which is defined in the appended claims.

What is claimed is:

1. A method for determining at least one characteristic of a treating chemistry inside a removable component having a graphic applied to the removable component in a laundry treating appliance having a controller, comprising:

applying a first intensity of light to the graphic and determining a corresponding first reflectance by said laundry treating appliance; and applying a second intensity of light to the graphic and determining a corresponding second reflectance, wherein the intensity of the second intensity light is greater than the intensity of the first intensity light and penetrates a surface of the graphic received by said laundry treating appliance; and determining at least one characteristic of the treating chemistry from the first and second reflectances by said controller.

2. The method of claim 1 wherein the first intensity of light has a different wavelength than the second intensity of light.

3. The method of claim 1 wherein the second intensity of light penetrates the graphic to reach at least a surface of the removable component.

4. The method of claim 3 wherein the second reflectance is indicative of the reflectance of the second intensity of light from the surface of the removable component.

5. The method of claim 1 wherein the second intensity of light penetrates the surface of the removable component and reaches the treating chemistry inside the removable component.

6. The method of claim 5 wherein the second reflectance is indicative of the reflectance of the second intensity of light from the treating chemistry inside the removable component.

7. The method of claim 1 wherein the first intensity of light penetrates an upper surface of the graphic to an interior of the graphic and the first reflectance is indicative of a reflectance from the interior of the graphic.

8. The method of claim 1 wherein the second intensity of light penetrates an upper surface of the graphic to an interior of the graphic and the second reflectance is indicative of the reflectance of the second intensity of light from the interior of the graphic.

9. The method of claim 1 wherein the second intensity of light penetrates more deeply into the graphic than the first intensity of light.

10. The method of claim 1 wherein the graphic comprises a label.

11. The method of claim 1 wherein the graphic comprises a substrate on which there is printed indicia.

12. The method of claim 11 wherein the first reflectance is from the printed indicia and the second reflectance is from the substrate.

13. The method of claim 1 wherein the at least one characteristic of the treating chemistry is at least one of: information indicative of a cycle of operation, information indicative of at least one operating parameter of a cycle of operation, a presence or absence of the treating chemistry, physical property of the treating chemistry, an amount of the treating chemistry, an identification of the treating chemistry and an authentication key.

14. The method of claim 1 wherein the treating chemistry comprises at least one of an enzyme, a surfactant, a bleach, a fabric softener, an oxidizing agent, a fragrance, wrinkle-reducing agent, an anti-static agent, a stain repellant, a water repellant, a shrinkage inhibitor, a color fidelity agent and mixtures thereof.

15. The method of claim 1 wherein at least one of the first intensity of light and the second intensity of light comprises light of multiple wavelengths.

16. The method of claim 15 wherein the multiple wavelengths comprise sequentially varying wavelengths.

17. The method of claim 1 wherein the first and second intensity of light have different polarity.

* * * * *